United States Patent [19]

Schwartz et al.

[11] Patent Number: 4,504,476

[45] Date of Patent: Mar. 12, 1985

[54] METHOD OF ADMINISTERING CALCIUM CHANNEL BLOCKING AGENTS

[76] Inventors: Arnold Schwartz; Ingrid L. Grupp; Gunter Grupp, all of University of Cincinnati, College of Medicine, 231 Bethesda Ave., Cincinnati, Ohio 45267; Alain de Pover, Klingentalgraben 7, 4057 Baesel, Switzerland

[21] Appl. No.: 532,662

[22] Filed: Sep. 16, 1983

[51] Int. Cl.³ .................... A61K 31/33; A61K 31/44
[52] U.S. Cl. .................................................. 514/211
[58] Field of Search .............................. 424/244, 263

[56] References Cited

U.S. PATENT DOCUMENTS 4,264,497  4/1981  Ohno et al. ........................ 424/244

OTHER PUBLICATIONS

Chem. Abst. 99:3563(r), (1983)–Andersson et al.
Chem. Abst. 99:64,033(q), (1983)–Glossman et al.
Chem. Abst. 99:115,596(k), (1983)–DePover et al.
Chem. Abst. 99:151,887(q), (1983)–Van Meel et al.
Chem. Abst. 99:205,834(r), (1983)–Van Meel et al.
Chem. Abst. 100:18032(e), (1984)–Conn et al.
Chem. Abst. 100:29610(t), (1984)–Spedding.

*Primary Examiner*—Douglas W. Robinson
*Attorney, Agent, or Firm*—Frost & Jacobs

[57] ABSTRACT

A method of potentiating the effect of a dihydropyridine derivative, such as nimodipine or nifedipine, by administering d-cis-diltiazem in an amount sufficient to inhibit calcium influx but insufficient to cause substantial decrease in contractility, and administering a dihydropyridine derivative in a submicromolar amount less than the dosage normally required for pharmacological effectiveness. A calcium channel blocking composition comprises a synergistic combination of d-cis-diltiazem and a dihydropyridine derivative.

8 Claims, 3 Drawing Figures

METHOD OF ADMINISTERING CALCIUM CHANNEL BLOCKING AGENTS

BACKGROUND OF THE INVENTION

This invention relates to a method of use of calcium channel blocking agents, and more particularly to a method of potentiating, i.e. augmenting synergistically, the pharmacological effects of dihydropyridine derivatives in cardiac tissue.

Calcium antagonists are relatively new drugs which are used to treat coronary heart disease. Their effects are to increase the flow of blood to the heart, remove stresses on the cardiovascular system, lower blood pressure and lower heartbeat. Administration of these drugs may prevent a heart attack.

Three calcium channel blocking agents are presently being used in the United States, known generically as nifedipine (a dihydropyridine derivative), verapamil (a papaverine derivative), and diltiazem (a 1,5 benzothiazepine derivative). Nifedipine is sold under the registered trademark PROCARDIA, verapamil under the registered trademarks ISOPTIN and CALAN, and diltiazem under the registered trademark CARDIZEM.

By way of further background, diltiazem is 3-acetoxy-2,3-dihydro-5-[2-(dimethylamino)ethyl]-2-(p-methyoxyphenyl)-1,5-benzothiazepin-4(5H)-one hydrochloride. It was developed in Japan. Due to the presence of two asymmetric carbon atoms, a d-cis isomer and an l-cis isomer are known to exist. The following molecular structure illustrates this isomerism:

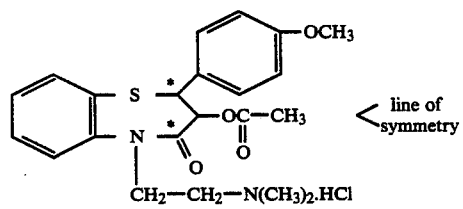

*asymmetric carbon atoms

In the d-cis isomer the side groups are oriented behind or below the plane of the benzothiazepine ring, whereas in the l-cis isomer the side groups are oriented above the ring. For convenience, the d-cis isomer, which is the active isomer in the method of this invention, will hereinafter be designated as "d-cis-diltiazem", and generic names of other drugs will be used.

The present invention constitutes a discovery that small dosages of d-cis-diltiazem potentiate the effects of nifedipine and other dihydropyridine derivatives and in the heart. This has very significant applications. Patients who are sensitive to nifedipine could take one-half or even one-quarter the normal dosage but receive the same benefits and additionally obtain the advantages of diltiazem as well. Diltiazem has an important antirhythm effect (i.e., prevents palpitations) which nifedipine lacks. Moreover, the combination of both drugs is believed to have a greater beneficial effect on high blood pressure than either drug alone. It will of course be recognized that smaller dosages of drugs also diminish greatly the chance of toxic side effects.

Numerous studies of the effects of calcium channel blocking agents have been reported in the literature. Reference may be made to "Symposium on Cardiovascular Disease and Calcium Antagonists", Arnold Schwartz, Guest Editor, *American Journal of Cardiology*, Vol. 49, No. 3, February 1982, pages 497–635, and articles acknowledged therein; and to "Calcium Channel-Blocking Drugs: A Novel Intervention for the Treatment of Cardiac Disease", Arnold Schwartz, Editor, *Circulation Research* Part II, Vol. 52, No. 2, February 1983, pages I-1 to I-174.

Reference may also be made to A. De Pover et al "Specific Binding Of [³H] Nitrendipine . . . Stimulation by Diltiazem", *Biochemical and Biophysical Research Communications*, Vol. 108, No. 1, September 1982, pages 110–117; and to an article by A. DePover et al in *Biochemical and Biophysical Research Communications*, Vol. 113, No. 1, May 1983, pages 185–191.

The molecular structures of nifedipine and verapamil are reported to be as follows:

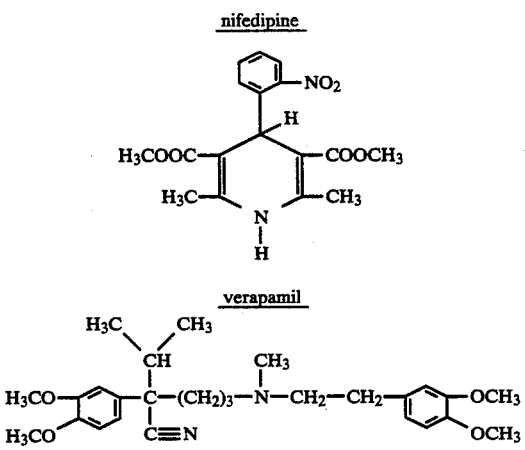

SUMMARY OF THE INVENTION

It is an object of the present invention to provide the beneficial effects of nifedipine and diltiazem while minimizing the possibility of toxic side effects.

According to the invention there is provided a method of stimulating the binding of a dihydropyridine derivative to cardiac tissue, which comprises administering an effective diltiazem isomer in combination with a dihydropyridine derivative, the diltiazem isomer being administered at a concentration insufficient to cause substantial decrease in contractility. More particularly, the present invention provides a method of potentiating the effect of a dihydropyridine derivative in producing negative inotropy in cardiac tissue, which comprises administering d-cis-diltiazem in an amount sufficient to inhibit calcium influx but insufficient to cause substantial decrease in contractility, and administering a dihydropyridine derivative in an amount less than the dosage thereof normally required for pharmacological effectiveness.

BRIEF DESCRIPTION OF THE DRAWING

Reference is made to the accompanying drawing wherein.

DETAILED DESCRIPTION

Nifedipine is a potent vasodilator which apparently acts by blocking calcium entry into arterial cells. It is also active on cardiac contraction and conduction, but much higher concentrations are required for this purpose than for relaxing arterial cells.

It has previously been suggested that the negative inotropic effect of nifedipine and other calcium antagonist drugs is due to specific blockage of "slow channels". A reversible, saturable and stereospecific binding process has also been reported. However, in cardiac muscle the dissociation constant ($K_D$) for binding is several orders of magnitude lower than the $I_{50}$ for inhibition of contraction or conduction, and it was therefore through to be doubtful that the specific membrane binding is related to the pharmacological receptor for dihydropyridines in the heart.

The data presented herein show the diltiazem stereospecifically stimulates [$^3$H] nimodipine (a nifedipine derivative) binding to a cardiac sarcolemmal preparation and specifically potentiates the effect of nimodipine in producing negative inotropy in isolated hearts. This new discovery therefore suggests that binding and pharmacological activity in heart are directly related.

Nimodipine is isopropyl-(2-methoxyethyl)-2,6-dimethyl-4-(3-nitrophenyl)-1,4-dihydropyridine-3,5-dicarboxylate.

Figure 1:
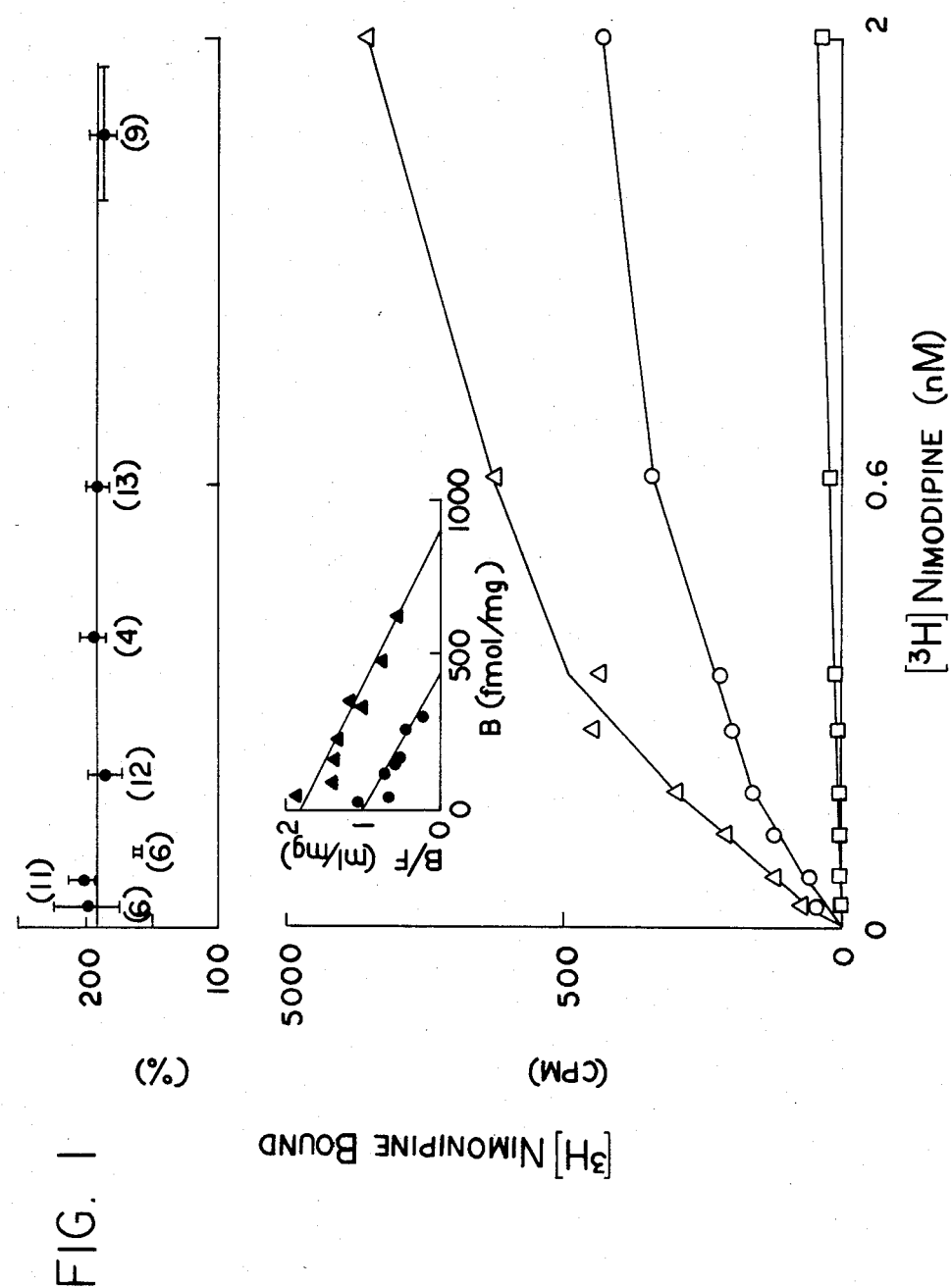
FIG. 1 is a graphic representation of the amount of nimodipine bound to cardiac membrane in the presence of diltiazem.

Referring to FIG. 1, it will be seen that diltiazem stimulates [$^3$H] nimodipine binding to cardiac sarcolemmal membranes by increasing the apparent number of binding sites. Although not wishing to be bound by theory it is believed that diltiazem can convert low affinity sites in cardiac membranes into high affinity sites, thus increasing the apparent number of the latter. Similar findings for skeletal muscle have previously been reported, but other reports on brain are contrary, suggesting rather an increase of affinity. Another possibility is that latent binding sites for nimodipine are rendered patent (open) by diltiazem.

Figure 2:
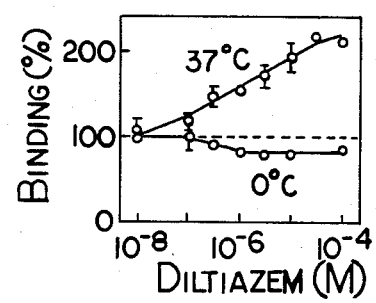
FIG. 2 is a graphic representation of the effect of various drugs on specific binding of nimodipine.
Figure 2:
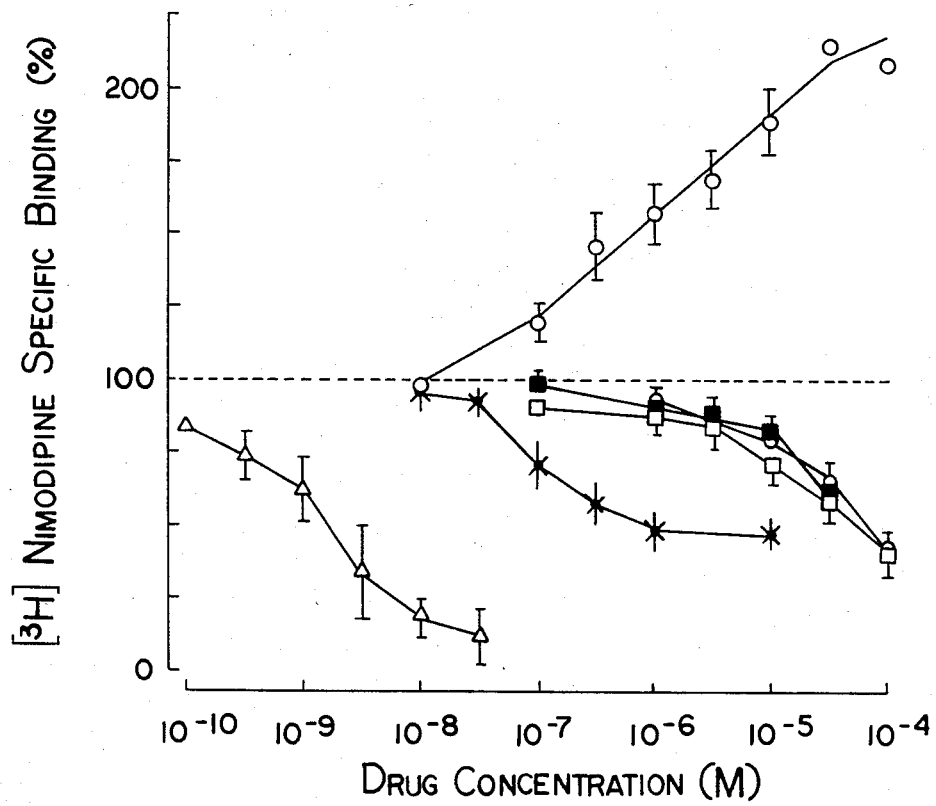

FIG. 2 indicates that stimulation of [$^3$H] nimodipine was produced by d-cis-diltiazem, but stimulation was not produced by nifedipine, by l-cis-diltiazem (a much less active isomer), by thiazesim (another diltiazem analogue), or by clonazepam, a related benzodiazepine. It is further shown in FIG. 2 that these drugs, except for nifedipine, affect [$^3$H] nimodipine binding at the same concentrations which depress cardiac contractility. Although there is thus a discrepancy between the effects of nifedipine on [$^3$H] nimodipine binding and on cardiac contractility, such a discrepancy does not occur with the other calcium entry blockers. The discrepancy thus appears to be specific for the dihydropyridine binding site. This prompted the hypothesis that a dihydropyridine low affinity site, i.e. the pharmacologically effective site, is converted into the high affinity site in the presence of diltiazem.

Figure 3:
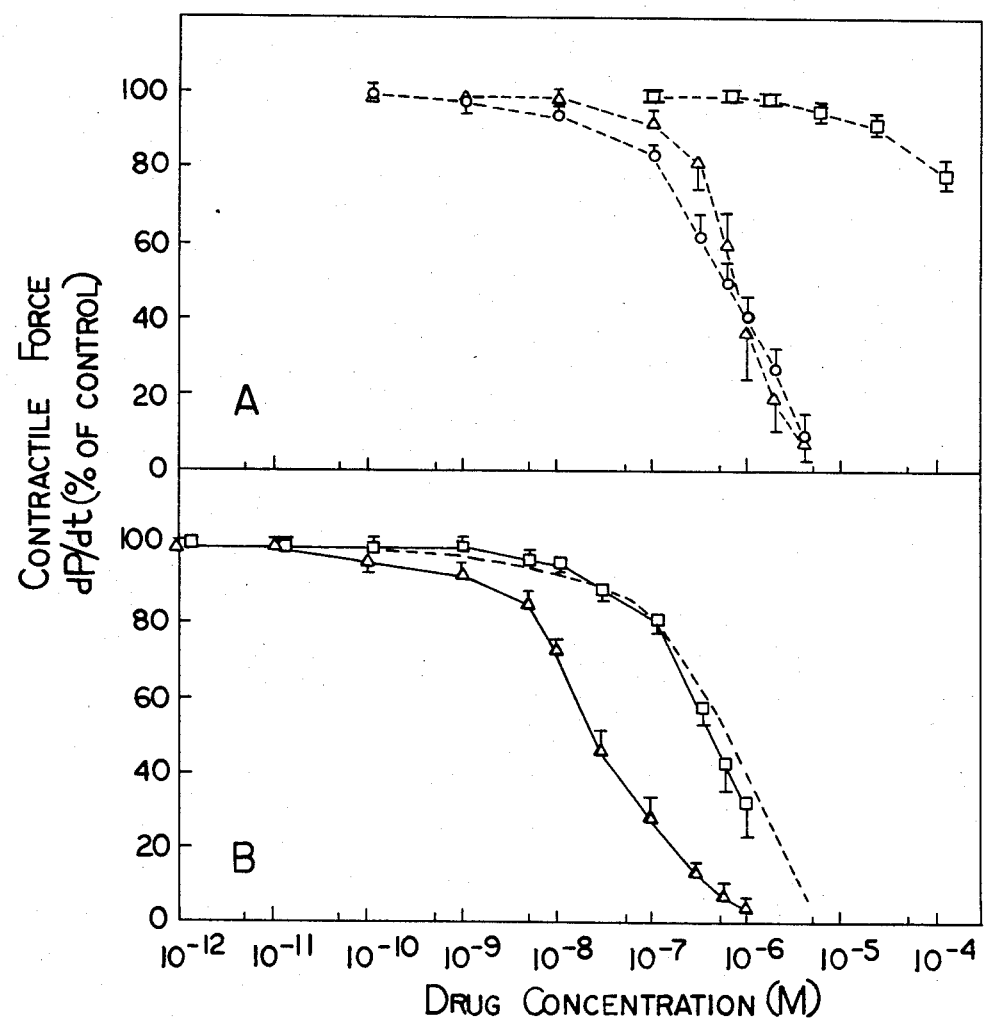
FIG. 3 is a graphic representation of contractile force vs. drug concentration.

Referring to FIG. 3, the effects are shown of nimodipine on contractility of retrogradely perfused rat hearts (Langendorff preparation) in the presence of d-cis-diltiazem (the active isomer), and l-cis-diltiazem (the much less active isomer). This cardiac preparation was used because it allows rapid diffusion of the drugs in the tissue and provides a stable base for contractility. Since both diltiazem and nimodipine depress contractility, only a low concentration of diltiazem, which produced only a slight decrease by itself, was administered. This concentration (250 nM), which was sufficient to stimulate [$^3$H] nimodipine binding significantly, drastically potentiated the negative inotropic response of nimodipine. The $I_{50}$ of nimodipine was shifted from $1.1 \times 10^{-6}$M to $3.3 \times 10^{-8}$M in the presence of d-cis-diltiazem. L-cis-diltiazem was ineffective under the same conditions.

It is pointed out that the $I_{50}$ values determined in these tests are not necessarily true $K_D$ values for receptor sites. However, it is believed that a shift in $I_{50}$ values represents a shift in $K_D$ also. If it is correct that d-cis-dilitiazem converts low affinity sites in nimodipine, it would be expected that, with the low concentration of diltiazem (250 nM) used in the tests of FIG. 3, only a relatively small number of nimodipine sites would be converted. The observed $I_{50}$ for nimodipine would be between 0.2 nM ($K_D$ for [$^3$H] nimodipine binding) and 1100 nM ($I_{50}$ in hearts not treated with diltiazem). The observed value of 33 nM is consistent with this hypothesis.

In the rat heart Langendorff preparation the negative inotropic response to diltiazem and nimodipine was fully reversible, the effects being washed out within 30 minutes. The potentiation of nimodipine response by diltiazem was also reversible, thus indicating that the conversion of low affinity to high affinity sites is reversible.

PREPARATIONS

FIG. 1—Membrane fractions of highly enriched in plasma membrane markers were prepared from dog ventricles according to Van Alstyne et al. 20–50 μg protein was incubated for 15 min at 37° C. in 1 ml medium containing 50 mM Tris-HCl (pH 7.4), different concentrations of [$^3$H] nimodipine (160 Ci/mmol) and in the absence (O) or the presence of $10^{-5}$M diltiazem (Δ) or of $10^{-6}$M nimodipine (□). The reaction was stopped by addition of 5 ml of ice-cold double-distilled water and filtration on Whatmann GF/F glass fiber filters. The filters were washed three times and the trapped radioactivity counted by liquid scintillation spectrometry. Specific binding was taken as the difference between control binding and the binding in the presence of unlabelled nimodipine (non-specific). Diltiazem was without effect on non-specific binding (not shown). The lower panel shows a typical experiment (triplicate determinations); the specific binding was analyzed according to Scatchard (Insert).

The upper panel shows the effect of diltiazem expressed as percentage of control specific binding in 4 to 13 different preparations (±S.E.M.).

FIG. 2—Dog heart membranes were incubated for 15 min at 37° C. in the presence of 0.17 nM [$^3$H] nimodipine, 50 mM Tris-HCl (pH 7.4) and the different concentrations of nifedipine (Δ), verapamil (X), d-cis-diltiazem (O), l-cis-diltiazem (●), thiazesim (□) or clonazepam (■). The specific binding was estimated as described in the legend to FIG. 1.

The insert plots a comparison of the effects of diltiazem on [$^3$H] nimodipine specific binding at 0° C. and 37° C. Incubation of 0° C. was carried out for 120 minutes. The influence of temperature may account for the absence of diltiazem-induced stimulation of [$^3$H] nitrendipine binding reported by others. Each drug was tested on 4 different membrane preparations (means ±S.E.M.).

FIG. 3—Wistar rats were anesthetized, the hearts quickly removed and perfused retrogradely through the aorta with oxygenated (95% $O_2$; 5% $CO_2$) Krebs-Henseleit solution at 37° C. (2 mM Ca++, 5.9 mM K0). The left ventricular pressure was recorded through a thin catheter and the transducer signal differentiated to record dP/dt. The heart was paced at a frequency about 20% above spontaneous heart rate (about 280 beats per min.). The perfusion pressure was adjusted to about 60 mm Hg. Coronary flow was continuously measured by weight with an electronic balance. After 30 min equilibration the drugs were infused at constant rate by Harvard infusion pumps through catheters inserted into the aortic tubing 10 cm above the heart. The $I_{50}$'s were estimated from each single curve and the mean $I_{50}$'s calculated from this data and not from the mean data plotted in this Figure. Upper graph: Cumulative dose response curves of nimodipine (O), $I_{50}$ $1.1 \pm 3.4 \times 10^{-6}$, N=11; d-cis-diltiazem (Δ), $I_{50}$ $8 \pm 2.5 \times 10^{-7}$M, n=3; l-cis-diltiazem (□), $I_{50} > 1.2 \times 10^{-4}$M, n=3. Lower graph. These hearts were continuously perfused with either $2.5 \times 10^{-7}$M d-cis-diltiazem (▲) or $5 \times 10^{-7}$M l-cis-diltiazem (■). Ten minutes after start of the diltiazem infusion, cumulative dose-response curves with nimodipine were obtained. The drug effects are expressed as percentage of dP/dt before drug infusion. $I_{50}$ of nimodipine in the presence of d-cis-diltiazem was $3.3 \pm 0.46 \times 10^{-8}$M, n=7, and in the presence of l-cis-diltiazem $7.3 \pm 2.2 \times 10^{-7}$M, n=3. The broken line indicates the nimodipine dose response curve (see upper graph) without diltiazem infusion.

Because both nimodipine and diltiazem occur in solid form, the drugs can be administered orally by consuming one pill of each drug in a physiologically effective dosage unit amount with the diltiazem being administered at a concentration insufficient to cause substantial decrease in contractility and with the nimodipine being administerered in an amount less than the normal therapeutic dosage. Of course, these drugs could be mixed together in their solid forms and made into tablet or capsule forms, or tablets of each drug could be produced and sandwiched together into one tablet as is well known to those skilled in the art. If desired, a coating could be applied to one of the components, e.g., nimodipine, to delay the release time. Also, the solids could be mixed with a suitable liquid carrier thus forming a solution which can be administered in liquid form as is commonly done. Further, both drugs can be mixed with a suitable carrier and injected intravenously in an effective dosage amount which is also well known to those skilled in the art.

We claim:

1. A method of stimulating the binding of a dihydropyridine derivative to cardiac tissue, which comprises administering d-cis-diltiazem in combination with a dihydropyridine derivative, said d-cis-diltiazem being administered at a submicromolar concentration insufficient to cause substantial decrease in contractility.

2. The method claimed in claim 1, wherein said dihydropyridine derivative is nimodipine, nitrendipine or nifedipine.

3. The method claimed in claim 2, wherein said nimodipine is administered in an amount less than the normal therapeutic dosage thereof.

4. A method of potentiating the effect of a dihydropyridine derivative in producing negative inotropy in cardiac tissue, which comprises administering d-cis-diltiazem in submicromolar amounts sufficient to inhibit calcium influx but insufficient to cause substantial decrease in contractility, and administering a dihydropyridine derivative in a submicromolar amount less than the dosage thereof normally required for pharmacological effectiveness.

5. The method claimed in claim 4, wherein said d-cis-diltiazem has the following molecular structure:

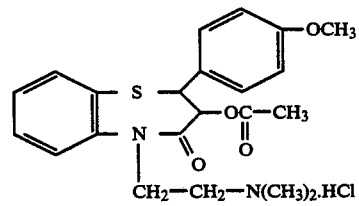

6. The method claimed in claim 4, wherein said dihydropyridine derivative is nimodipine, nitrendipine or nifedipine.

7. A calcium channel blocking composition comprising, in synergistic combination, d-cis-diltiazem in combination with a dihydropyridine derivative, said d-cis-diltiazem being administered in a submicromolar concentration sufficient to cause substantial decrease in contractility.

8. The composition claimed in claim 7, wherein said dihydropyridine derivative is nimodipine, nitrendipine or nifedipine.

* * * * *